(12) United States Patent
Mizuno et al.

(10) Patent No.: US 6,542,691 B2
(45) Date of Patent: Apr. 1, 2003

(54) GLASS CAPILLARY ARRAY FOR FLUORESCENCE ANALYSIS AND MANUFACTURING METHOD THEREOF

(75) Inventors: Toshiaki Mizuno, Tokyo (JP); Akihiko Hattori, Osaka (JP); Takehiko Kitamori, Tokyo (JP)

(73) Assignee: Nippon Sheet Glass Co., Ltd., Osaka (JP)

( * ) Notice: Subject to any disclaimer, the term of this patent is extended or adjusted under 35 U.S.C. 154(b) by 0 days.

(21) Appl. No.: 10/039,501

(22) Filed: Oct. 25, 2001

(65) Prior Publication Data

US 2002/0102091 A1 Aug. 1, 2002

(30) Foreign Application Priority Data

Oct. 27, 2000 (JP) ........................................ 2000-328883

(51) Int. Cl.⁷ ................................................ G02B 6/10
(52) U.S. Cl. ...................... 385/146; 385/115; 356/344; 250/458.1; 250/461.2; 204/455; 204/451
(58) Field of Search .......................... 385/12, 115, 146, 385/147; 356/344; 250/458.1, 461.2; 204/455, 451; 359/618

(56) References Cited

U.S. PATENT DOCUMENTS

| | | | |
|---|---|---|---|
| 5,324,401 A | * | 6/1994 | Yeung ...................... 204/180.1 |
| 5,582,705 A | * | 12/1996 | Yeung ........................ 204/603 |
| 6,039,925 A | * | 3/2000 | Nemoto ...................... 356/344 |
| 6,404,495 B1 | * | 6/2002 | Melman ...................... 356/344 |

FOREIGN PATENT DOCUMENTS

JP         09-152418 A      6/1997

OTHER PUBLICATIONS

"DNA Analysis", Bunseki, Jan. 1999 edition, pp. 25–33.
"Multiple Sheath–Flow Capillary–Array Electrophoresis for Multicolor Fluorescent DNA Detection", Analytical Chemistry, vol. 66, No. 7, Apr. 1, 1994, pp. 1021–1026.

* cited by examiner

Primary Examiner—Audrey Chang
Assistant Examiner—Leo Boutsikaris
(74) Attorney, Agent, or Firm—Frishauf, Holtz, Goodman & Chick, P.C.

(57) ABSTRACT

A glass capillary array for fluorescence analysis is provided which is capable of preventing reduction of the transmittance of a laser beam through the glass capillaries during electrophoretic DNA fluorescence analysis, and a method of manufacturing the glass capillary array. The glass capillary array for fluorescence analysis is comprised of a plurality of glass capillaries each having a rectangular cross section and having an internal hole formed therein, and arranged in a row along a direction of irradiation of a laser beam for fluorescence analysis. The glass capillary array has a fluorescence analysis section comprising a portion of each of the glass capillaries positioned in a region including an optical axis of the laser beam and a vicinity thereof, and the glass capillaries are joined together substantially into a single body using a transparent material in at least the fluorescence analysis section.

11 Claims, 6 Drawing Sheets

GLASS CAPILLARY ARRAY FOR FLUORESCENCE ANALYSIS AND MANUFACTURING METHOD THEREOF

BACKGROUND OF THE INVENTION

1. Field of the Invention

The present invention relates to a glass capillary array for fluorescence analysis and a manufacturing method thereof.

2. Prior Art

Fluorometric gel electrophoresis is widely used as a DNA fluorescence analysis method for gene analysis and the like. Electrophoresis has the advantages that, since real time detection is carried out using laser-excited fluorescence, both the sensitivity and the throughput are high. Various fluorescent substances suitable for use in electrophoresis have been developed (see, for example, "Bunseki" ("Analysis"), January 1999 edition, pages 25–33). DNA fluorescence analysis using electrophoresis is carried out by separating fluorescently labeled DNA fragments according to molecular weight using gel electrophoresis, irradiating the DNA fragments with a laser beam and detecting the fluorescence thus emitted by the fluorescent labels, and analyzing a succession of detection signals obtained.

In a conventional analyzer that uses electrophoresis, an array of glass capillaries each having a circular cross section passes through an optical cell filled with a buffer solution, and DNA fragments that migrate through the glass capillary array are analyzed using a laser beam. To minimize background light due to scattering, the glass capillaries are arranged in a single row along the direction of the horizontally irradiated laser beam.

However, with such an analyzer, because the glass capillaries have a circular cross section, the laser beam is scattered at the surface of the first glass capillary, and hence cannot be irradiated uniformly onto the following glass capillaries.

To combat this problem, either the glass capillaries are given a square cross section so that the angle of incidence of the laser beam on each of the glass capillaries is always zero and hence the influence of refraction of the laser beam is eliminated, or else the portion of the glass capillary array irradiated by the laser beam is removed so as to form buffer solution sheath flows. A device disclosed in Japanese Laid-open Patent Publication (Kokai) No. 9-152418 provides an example of the former, and a device disclosed in Anal. Chem., 1994, Vol. 66, pages 1021–1026 provides an example of the latter.

However, in the case of the device disclosed in Japanese Laid-open Patent Publication (Kokai) No. 9-152418, there are spaces between the glass capillaries, and hence the laser beam used in the measurement is scattered at the surface of each glass capillary, resulting in the intensity of the laser beam progressively decreasing as the laser beam passes through each glass capillary, and hence in there being a limit on the number of glass capillaries on which measurement can be carried out simultaneously.

Moreover, in the case of the device disclosed in Anal. Chem., 1994, Vol. 66, pages 1021–1026, a special buffer solution is required, and the structure of the analyzer is complicated.

SUMMARY OF THE INVENTION

It is an object of the present invention to provide a glass capillary array for fluorescence analysis which is capable of preventing reduction of the transmittance of a laser beam through the glass capillaries during electrophoretic DNA fluorescence analysis, and a method of manufacturing the glass capillary array.

To attain the above object, the present invention provides a glass capillary array for fluorescence analysis, comprising a plurality of glass capillaries each having a rectangular cross section and having an internal hole formed therein, the plurality of glass capillaries being arranged in a row along a direction of irradiation of a laser beam for fluorescence analysis, wherein the glass capillary array has a fluorescence analysis section comprising a portion of each of the glass capillaries positioned in a region including an optical axis of the laser beam and a vicinity thereof, and the glass capillaries are joined together substantially into a single body using a transparent material in at least the fluorescence analysis section.

With the above arrangement, reduction of the transmittance of the laser beam through the glass capillaries during electrophoretic DNA fluorescence analysis can be prevented.

Preferably, the difference between the refractive index of the transparent material and the refractive index of the mother glass of the glass capillaries is not more than 0.3. As a result, reduction of the transmittance of the laser beam through the glass capillaries can be prevented reliably.

More preferably, the above refractive index difference is not more than 0.3, and the number of glass capillaries joined together is in a range of 10 to 30. As a result, reduction of the transmittance of the laser beam through the glass capillaries can be prevented more reliably.

Alternatively, the above refractive index difference is not more than 0.2, and the number of glass capillaries joined together is in a range of 10 to 100. As a result, reduction of the transmittance of the laser beam through the glass capillaries can be prevented more reliably.

Preferably, the glass capillaries are joined together using a resin adhesive. As a result, the glass capillaries can be joined together easily.

Alternatively, the glass capillaries are joined together using glass frit. As a result, the glass capillaries can be joined together easily.

Alternatively, the glass capillaries are joined together by welding using a laser beam. As a result, the glass capillaries can be joined together reliably, and the difference between the refractive index of the transparent material and the refractive index of the glass capillaries can be made substantially zero.

To attain the above object, the present invention further provides a method of manufacturing a glass capillary array for fluorescence analysis, comprising the steps of arranging a plurality of glass capillaries, each having a rectangular cross section and having an internal hole formed therein, in a row along a direction of irradiation of a laser beam for fluorescence analysis, to form a glass capillary array having a fluorescence analysis section comprising a portion of each of the glass capillaries positioned in a region including an optical axis of the laser beam and a vicinity thereof, and joining the glass capillaries together substantially into a single body using a transparent material in at least the fluorescence analysis section.

With the above arrangement, reduction of the transmittance of the laser beam through the glass capillaries during electrophoretic DNA fluorescence analysis can be prevented.

Preferably, the glass capillaries are joined together using a resin adhesive. As a result, the glass capillaries can be joined together easily.

Alternatively, the glass capillaries are joined together using glass frit. As a result, the glass capillaries can be joined together easily.

Alternatively, the glass capillaries are joined together by welding using a laser beam. As a result, the glass capillaries can be joined together reliably, and the difference between the refractive index of the transparent material and the refractive index of the glass capillaries can be made substantially zero.

The above and other objects, features and advantages of the invention will become more apparent from the following detailed description taken in conjunction with the accompanying drawings.

BRIEF DESCRIPTION OF THE DRAWINGS

FIG. 6A is a longitudinal sectional view;

FIG. 6B is a cross-sectional view;

FIG. 7A is a longitudinal sectional view;

FIG. 7B is a cross-sectional view; and

DETAILED DESCRIPTION OF PREFERRED EMBODIMENTS

A description will now be given of the constitution of a DNA analyzer that uses a glass capillary array for fluorescence analysis according to an embodiment of the present invention, with reference to the drawings.

Figure 1:
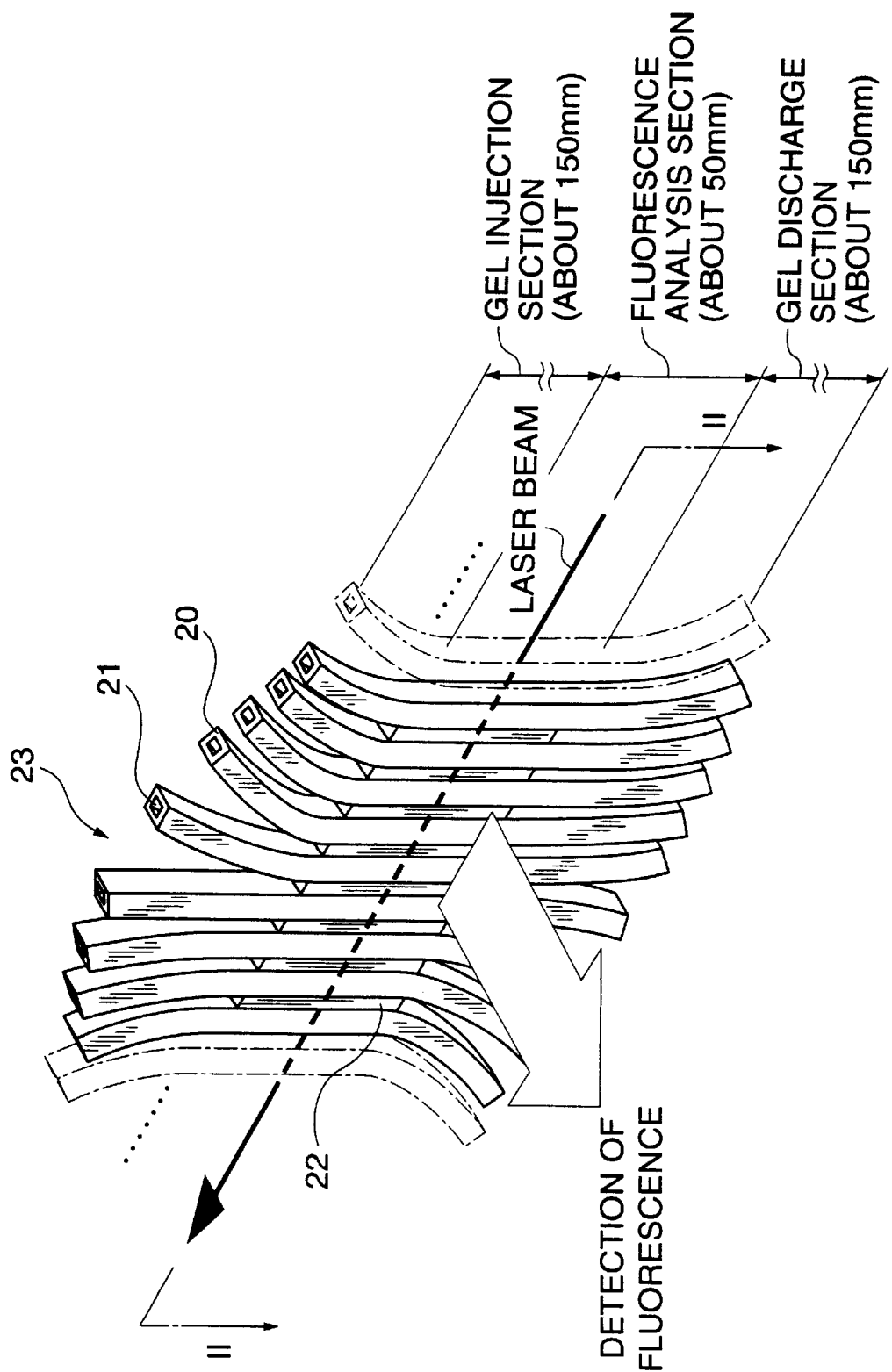
FIG. 1 is a perspective view showing principal parts of a DNA analyzer that uses a glass capillary array for fluorescence analysis according to an embodiment of the present invention.
Figure 2:
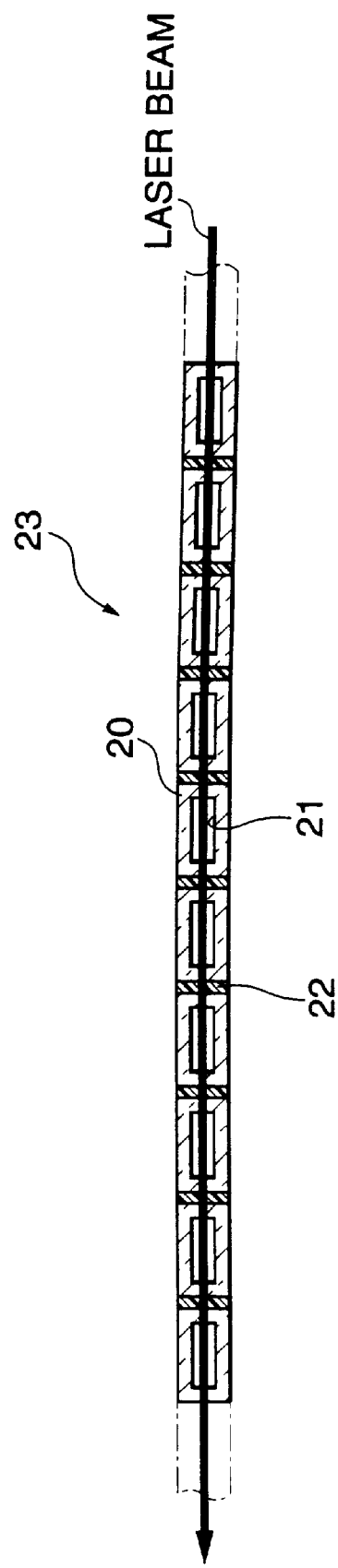
FIG. 2 is a sectional view taken along line II—II in FIG. 1.

FIG. 1 is a perspective view showing principal parts of a DNA analyzer that uses a glass capillary array for fluorescence analysis according to an embodiment of the present invention. FIG. 2 is a sectional view taken along line II—II in FIG. 1.

In FIG. 1, the glass capillary array 23 is comprised of a plurality of, for example 100, vertically oriented glass capillaries 20 for fluorescence analysis. The glass capillaries 20 are arranged in a single row with a pitch of 0.35 mm along the direction of irradiation of a laser beam for fluorescence analysis; the laser beam, described later, is irradiated horizontally. Each glass capillary 20 has an oblong cross section, and has formed therein along the longitudinal axis thereof a narrow internal hole 21 having an oblong cross section. The cross-sectional shapes of the glass capillary 20 and the internal hole 21 will be described in detail later with reference to FIGS. 6A and 6B and FIGS. 7A and 7B.

The long sides of the cross section of the internal hole 21 and the long sides of the cross section of the glass capillary 20 are parallel to one another, and these long sides are oriented in the direction in which the glass capillaries 20 are lined up. The internal hole 21 may alternatively have a circular cross section as described later.

The glass capillary array 23 is comprised of a gel injection section, a fluorescence analysis section, and a gel discharge section. The fluorescence analysis section is positioned in a region including the optical axis of the laser beam for fluorescence analysis, described later, and the vicinity thereof. In the present embodiment, the fluorescence analysis section is at a central level of the glass capillary array 23, and portions of the glass capillaries 20 in the fluorescence analysis section are joined together using a joining method, described later, for example a resin adhesive 22. The gel injection section is comprised of a portion of the glass capillary array 23 above the fluorescence analysis section, and the gel discharge section is comprised of a portion of the glass capillary array 23 below the fluorescence analysis section. In the present embodiment, the length of the gel injection section of the glass capillary array 23 is about 150 mm, the length of the fluorescence analysis section is about 50 mm, and the length of the gel discharge section is about 150 mm.

DNA fluorescence analysis is carried out by filling the glass capillaries 20 with a gel, separating fluorescently labeled DNA fragments according to molecular weight using gel electrophoresis, irradiating the DNA fragments with a laser beam and detecting the fluorescence thus emitted from the fluorescent labels, and analyzing a succession of detection signals obtained.

There are no particular limitations on the composition or material of the glass capillaries 20, but considering that the glass capillaries 20 are to be used for analysis, this material is preferably a transparent glass having high acid resistance and alkali resistance, although a transparent material having acid resistance and alkali resistance other than a glass such as a resin may also be used.

When the glass capillaries 20 are made of glass, the mother glass may be preferably silicate glass, for example, a quartz glass (refractive index 1.46), Pyrex (proprietary name of an aluminosilicate glass made by Corning Glass Works) glass (refractive index 1.47), a soda lime silicate glass (refractive index 1.52), an aluminoborosilicate glass, an alkali-free glass, a borosilicate glass, or the like. Of these, the soda lime silicate glass is manufactured by the float process and used as ordinary window glass in buildings.

The above silicate glass preferably has a composition containing at least 45 mass % of $SiO_2$. As a result, chemical resistance such as resistance to organic solvents, acid washing and alkali washing can be improved, and the transparency in the ultraviolet region can also be improved.

More preferably, the composition of the above silicate glass is 45 to 80 mass % of $SiO_2$, 1 to 20 mass % of $Al_2O_3$, 5 to 30 mass % of RO (MgO, CaO, SrO, BaO, ZnO), and 4 to 14 mass % of $R_2O$ ($Na_2O$, $K_2O$, $Li_2O$). As a result, the chemical resistance as described above can be improved, and the formability, i.e. workability, drawability etc., of the glass elements used in manufacturing the glass capillaries can be improved.

Moreover, the above-mentioned RO preferably consists of 0 to 8 mass % of MgO, 0 to 10 mass % of CaO, 0 to 10 mass % of SrO, 0 to 30 mass % of BaO, and 0 to 4 mass % of ZnO.

The gel filled into the glass capillaries 20 is not usually strongly acidic or strongly alkaline, and hence a soda lime silicate glass or the like will have sufficient chemical resistance to be used as the glass capillaries 20. Except in the case of an alkali-free glass, the glass is preferably subjected to chemical strengthening by an ion exchange method.

Methods of joining the glass capillaries 20 of the glass capillary array 23 together in the fluorescence analysis section to form a single body will now be described.

Examples of joining methods are joining using a resin adhesive, joining using glass frit, and joining by welding with a laser beam.

Moreover, in the present invention, the glass capillaries 20 may be joined together not only in the fluorescence analysis section but also in the gel injection section and/or the gel discharge section.

(1) Joining using a resin adhesive

From the standpoint of reducing reflection loss at the interfaces between the resin adhesive and the glass capillaries 20, the resin adhesive preferably has a refractive index close to that of the glass capillaries 20. Moreover, the resin adhesive is preferably transparent in the visible region (wavelength: 480 to 700 nm).

An organic type adhesive, an inorganic type adhesive, a sol-gel solution or the like can be used as the resin adhesive; a liquid reaction type adhesive such as an epoxy resin, an unsaturated ester resin, a phenol resin or a chloroprene resin can be used, or an instant adhesive such as a cyanoacrylate resin or a diacrylate resin can be used. The refractive indexes of such resin adhesives are in a range of 1.3 to 1.6, and hence the resin adhesive to be used can be selected as appropriate considering the refractive index of the glass capillaries 20.

For example, to make the difference between the refractive index of the glass capillaries 20 and the refractive index of the resin adhesive about 0.1, Pyrex glass can be used as the glass capillaries 20 and an epoxy resin as the resin adhesive. To make the refractive index difference about 0.2, Pyrex glass can be used as the glass capillaries 20 and a cyanoacrylate resin as the resin adhesive. To make the refractive index difference substantially zero, quartz glass can be used as the glass capillaries 20 and an epoxy resin adhesive can be used as the resin adhesive.

Figure 3:
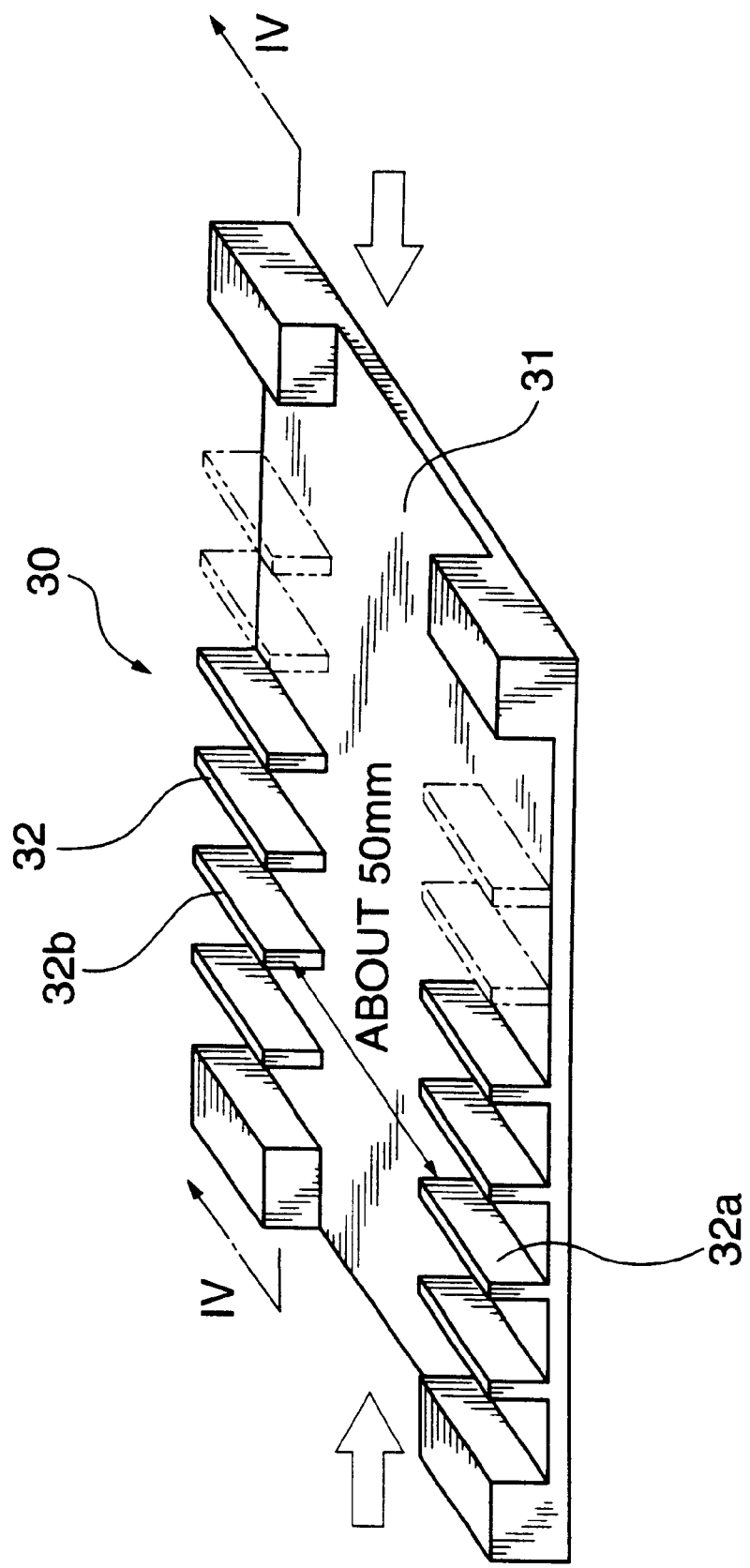
FIG. 3 is a perspective view of an arranging jig for glass capillaries 20.
Figure 4:
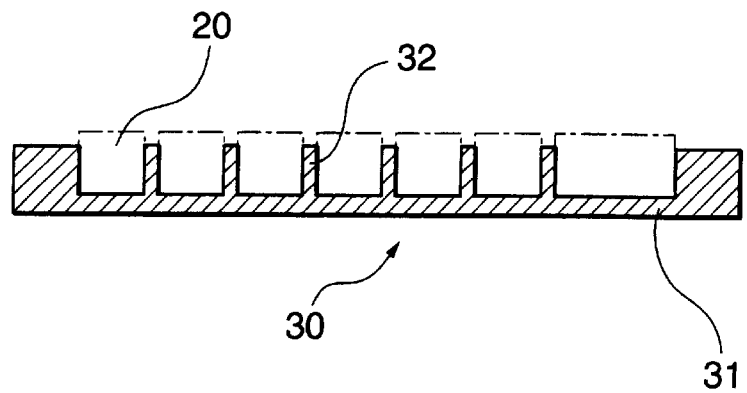
FIG. 4 is a sectional view taken along line IV—IV in FIG. 3.

Joining of the glass capillaries 20 using the resin adhesive is carried out using an arranging jig for the glass capillaries 20 as shown in FIGS. 3 and 4. FIG. 3 is a perspective view of the arranging jig for the glass capillaries 20, and FIG. 4 is a sectional view taken along line IV—IV in FIG. 3.

In FIG. 3, the arranging jig 30 is comprised of a horizontally disposed baseplate 31, and a plurality of pairs of partitioning plates 32 provided at equal intervals on the upper surface of the baseplate 31, with the length of the gaps between the partitioning plates 32 corresponding to the length of the long sides of the cross section of a glass capillary 20. The gap between partitioning plates 32a and 32b, which together make up a pair, is about 50 mm, corresponding to the length of the fluorescence analysis section.

The glass capillaries 20 are arranged between the partitioning plates 32 of the arranging jig 30 as shown in FIG. 4, and then the resin adhesive 22 is applied into the gaps between the glass capillaries 20. The range over which the resin adhesive is applied in the length direction of the glass capillaries 20 is about 50 mm, corresponding to the length of the fluorescence analysis section.

Moreover, pressure is applied to the group of glass capillaries 20 from both sides of the arranging jig 30 as shown by the arrows in FIG. 3, thus compression bonding the glass capillaries 20 together.

According to the joining method described above, the glass capillaries 20 are joined together into a single body using a resin adhesive, and hence the glass capillaries 20 can be joined together into a single body easily.

A description will now be given of criteria for selecting the resin adhesive.

In a DNA analyzer, the glass capillary array 23 is composed of about 100 glass capillaries 20. In this case, the laser beam passes through all of the glass capillaries 20. Every time the laser beam passes from a glass capillary 20 into the resin adhesive or from the resin adhesive into a glass capillary 20, i.e. every time the laser beam passes through an interface between a glass capillary 20 and the resin adhesive, the power of the transmitted laser beam drops due to reflection, and hence the transmittance of the laser beam falls progressively with distance from the laser source as shown in Table 1. The intensity of the fluorescence from each glass capillary 20 measured in the fluorescence analysis is proportional to the transmittance of the laser beam.

TABLE 1

| Refractive index difference | Laser beam transmittance (%) Capillary No. | | | | |
| --- | --- | --- | --- | --- | --- |
| Δn | 10th | 30th | 50th | 70th | 100th |
| 0.0 | 92 | 92 | 92 | 92 | 92 |
| 0.1 | 90 | 87 | 84 | 80 | 76 |
| 0.2 | 84 | 69 | 56 | 46 | 34 |
| 0.3 | 74 | 46 | 28 | 17 | 8 |

The refractive index difference $\Delta n$ ($=n_g-n_r$) between the refractive index $n_g$ of the glass capillaries 20 and the refractive index $n_r$ of the resin adhesive was varied from 0 to 0.3, and the transmittance of the laser beam at the 10th, 30th, 50th, 70th, and 100th capillaries was measured. The results are shown in Table 1.

Considering that the transmittance of the laser beam should not be allowed to drop below 30%, it can be seen from Table 1 that it is preferable to select the resin adhesive in accordance with the following criteria.

The difference between the refractive index of the resin adhesive and the refractive index of the mother glass of the glass capillaries 20 is preferably no more than 0.3. When this refractive index difference is 0.3 or less, the number of glass capillaries 20 joined together is preferably in a range of 10 to 30. When the refractive index difference is 0.2 or less, the number of glass capillaries 20 joined together is preferably in a range of 10 to 100.

(2) Joining using low-melting-point glass frit

In this method, commercially sold low-melting-point glass frit is used as a bonding agent. The joining of the glass capillaries 20 using the low-melting-point glass frit is carried out using the arranging jig 30 shown in FIGS. 3 and 4, as in the case of the resin adhesive described above.

The glass capillaries 20 are arranged between the partitioning plates 32 of the arranging jig 30 as shown in FIG. 4, and then the low-melting-point glass frit is applied into the gaps between the glass capillaries 20. The range over which the low-melting-point glass frit is applied in the length direction of the glass capillaries 20 is about 50 mm, corresponding to the length of the fluorescence analysis section.

Moreover, pressure is applied to the group of glass capillaries 20 from both sides of the arranging jig 30 as shown by the arrows in FIG. 3 while heating to the melting point of the low-melting-point glass frit, thus compression bonding the glass capillaries 20 together.

According to the joining method described above, the glass capillaries 20 are joined together into a single body using low-melting-point glass frit, and hence the glass capillaries 20 can be joined together into a single body easily.

Examples of low-melting-point glass frits are ones based on a $B_2O_3$—PbO—ZnO system or a $B_2O_3$—PbO—$Bi_2O_3$ system. Specifically, the glass frits shown as Examples 1 to 5 in Table 2 are preferable.

TABLE 2

| | Example | | | | | Units: mol % |
|---|---|---|---|---|---|---|
| | 1 | 2 | 3 | 4 | 5 | |
| $B_2O_3$ | 30.4 | 30 | 30 | 30 | 30 | |
| PbO | 69.5 | 60 | 60 | 50 | 35 | |
| ZnO | | 10 | | | | |
| $Bi_2O_3$ | | | 10 | | | |
| $TiO_2$ | | | | 20 | 35 | |

(3) Joining by welding with a laser beam

Figure 5:
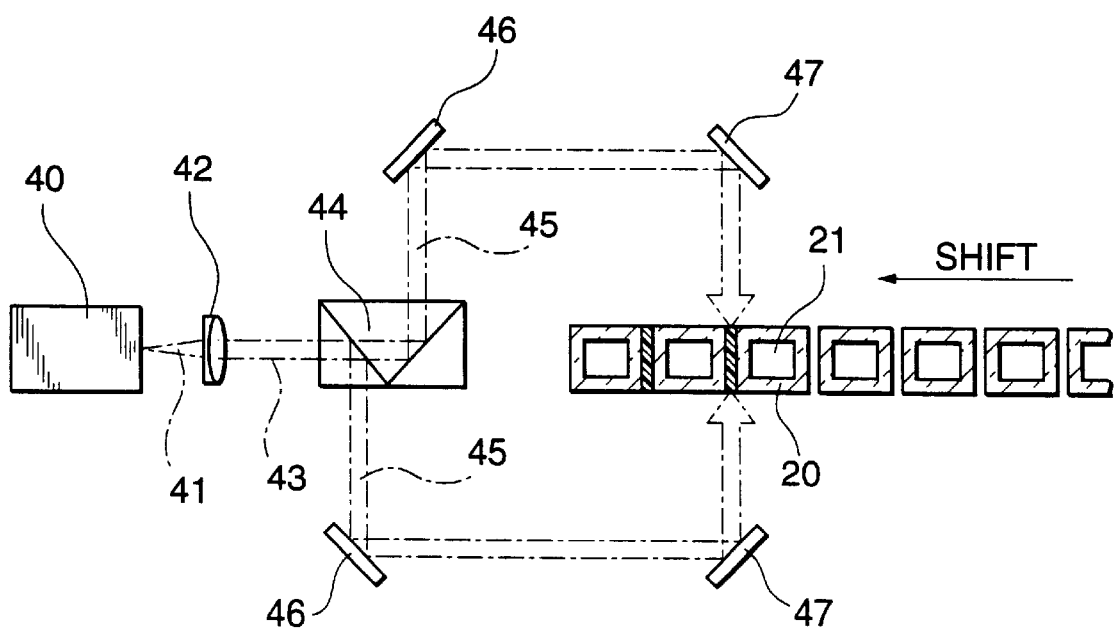
FIG. 5 is a diagram useful in explaining a laser beam irradiation apparatus for welding glass capillaries 20 together.

In this method, a laser beam irradiation apparatus such as that shown in FIG. 5 is used. In FIG. 5, a laser oscillator 40 emits a laser beam 41, the laser beam 41 is made into a parallel beam 43 of a predetermined diameter using a collimator 42, the parallel beam 43 is then split into two laser beams 45 traveling in opposite directions to one another using a splitter 44, and the laser beams 45 are irradiated via mirrors 46 and 47 from each side of a gap (about 50 μm) between glass capillaries 20 while scanning over a predetermined length.

The laser beams 45 irradiated from each side of the gap between the glass capillaries 20 reach right into the gap, thus melting and hence bonding together the glass capillaries 20.

At this time, a plurality of glass capillaries 20 are held in a suitable jig with gaps of about 50 μm between each glass capillary 20 and the next, and welding is carried out in each of the gaps by laser beam irradiation as described above, with shifting from each gap to the next being carried out using a suitable shifting apparatus.

A laser source such as the laser oscillator 40 of the embodiment described above is suitable as the heat source for welding the glass capillaries 20 together, since in this case a large energy density can be obtained easily and heating with a good energy efficiency is possible. In particular, a $CO_2$ laser, a YAG laser or an Ar laser is preferable.

If the wavelength of the laser beams 45 emitted from the laser oscillator 40 is too long, then the energy will be too low and it may not be possible to melt the glass capillaries 20 sufficiently. If, on the other hand, the wavelength is too short, then the energy will be too high and the glass capillaries 20 may fracture. The wavelength is thus preferably in a range of 250 to 20,000 nm, more preferably 500 to 12,000 nm.

Moreover, it is not desirable to make the energy density of the laser beams 45 emitted from the laser oscillator 40 too high, since then the heating rate will be high and there will be a risk of the glass capillaries 20 being damaged by heat shock. If, on the other hand, the energy density is too low, then the temperature of the glass may not be raised sufficiently. The energy density is thus preferably in a range of 1 to 100 W/mm$^2$, more preferably 2 to 80 W/mm$^2$.

According to the joining method described above, the glass capillaries 20 are joined together into a single body by welding with a laser beam, and hence the glass capillaries 20 can be joined together into a single body reliably, and moreover the difference between the refractive index of the glass capillaries 20 and the refractive index in the gaps therebetween can be made substantially zero.

In the joining methods (1) to (3) described above, to maintain the strength and parallelity of the glass capillary array 23 after the glass capillaries 20 have been joined together, the glass capillary array 23 may be fixed using a backing plate, not shown in the drawings.

Moreover, the glass capillary array 23 is not necessarily comprised of a single row of glass capillaries 20, but may alternatively be comprised of a plurality of rows of glass capillaries 20.

FIGS. 6A and 6B and FIGS. 7A and 7B are views useful in explaining possible cross-sectional shapes of each glass capillary 20 and the internal hole 21 formed therein.

Figure 6A:
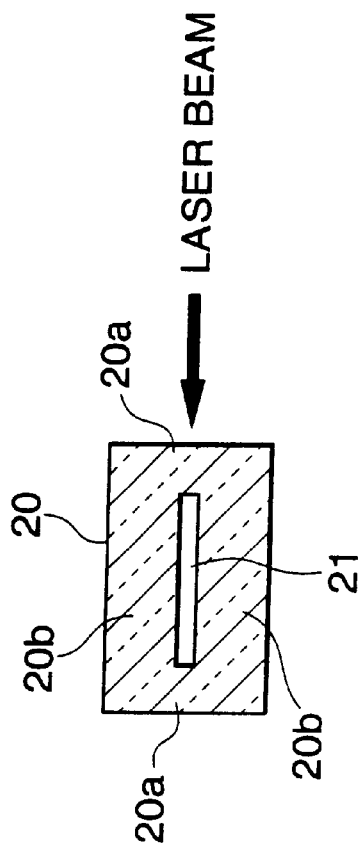
FIGS. 6A and 6B are views useful in explaining the cross-sectional shapes of a glass capillary 20 and an internal hole 21 formed therein; specifically.
Figure 6B:
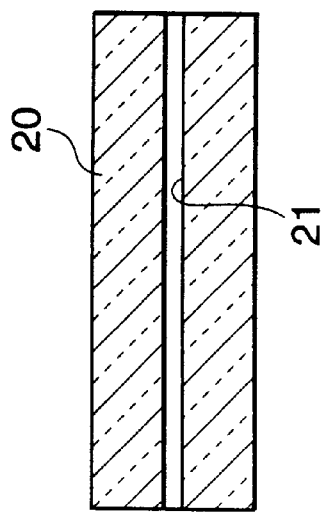

FIGS. 6A and 6B show a case in which the glass capillary 20 has an oblong cross section, the internal hole 21 has an oblong cross section, and the internal hole 21 is positioned in the center of the glass capillary 20 in the direction of the short sides of the cross section of the internal hole 21. In this case, thin-walled portions 20a formed along the direction of the short sides of the cross section of the internal hole 21 are positioned in the path of the laser beam and hence absorption loss of the laser beam is reduced, and thick-walled portions 20b formed along the direction of the long sides of the cross section of the internal hole 21 act as strengthening portions.

Figure 7A:
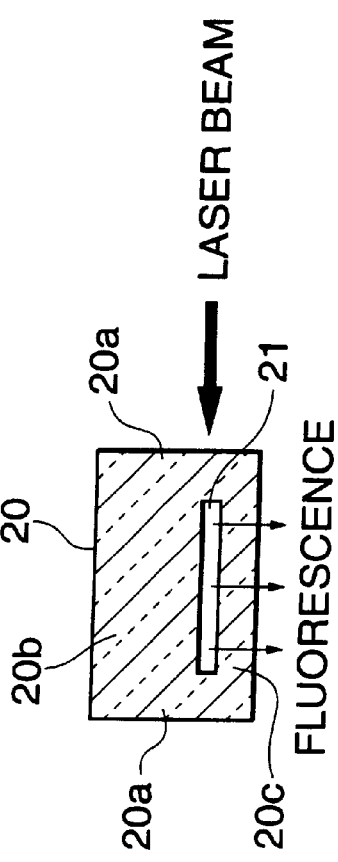
FIGS. 7A and 7B are views useful in explaining the cross-sectional shapes of a glass capillary 20 and an internal hole 21 formed therein; specifically.
Figure 7B:
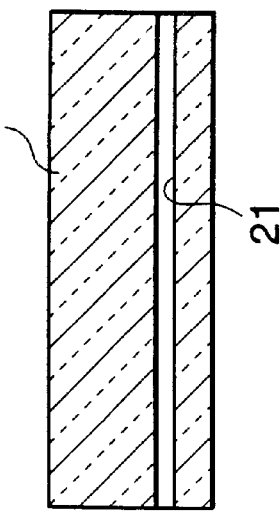

FIGS. 7A and 7B show a case in which the glass capillary 20 has an oblong cross section, the internal hole 21 has an oblong cross section, and the internal hole 21 is offset from the center of the glass capillary 20 in the direction of the short sides of the cross section of the internal hole 21. In this case, thin-walled portions 20a formed along the direction of the short sides of the cross section of the internal hole 21 are positioned in the path of the laser beam and hence absorption loss of the laser beam is reduced. Moreover, a thin-walled portion 20c formed along the direction of a long side of the cross section of the internal hole 21 is positioned in the path of the fluorescence from the DNA fragments caused by the laser beam irradiation and hence absorption loss of this fluorescence is reduced, and a thick-walled portion 20b formed along the direction of a long side of the cross section of the internal hole 21 acts as a strengthening portion.

There are no particular limitations on the dimensions of the glass capillary 20 shown in FIGS. 6A and 6B and the glass capillary 20 shown in FIGS. 7A and 7B, but the glass capillary 20 has, for example, a length of 50 to 300 mm, the cross section of the glass capillary 20 has, for example, long sides of length 50 to 300 μm and short sides of length 25 to 150 μm, and the cross section of the internal hole 21 has, for example, long sides of length 40 to 260 μm and short sides of length 15 to 130 μm. Regarding the glass capillary 20 shown in FIGS. 7A and 7B, the amount of offset of the internal hole 21 from the center of the glass capillary 20 is, for example, 10 to 30 μm.

With the glass capillary 20 shown in FIGS. 6A and 6B and the glass capillary 20 shown in FIGS. 7A and 7B, the ratio of the cross-sectional area of the internal hole 21 to the cross-sectional area of the glass capillary 20 is preferably 25 to 90%. If this ratio is less than 25%, then the glass portions become too thick, and hence the absorption loss when a laser beam is irradiated through a plurality of glass capillaries 20 arranged in a row becomes large. If this ratio is more than 90%, on the other hand, then the glass portions become too thin, and hence the strength of the glass capillary 20 drops.

With the glass capillary 20 shown in FIGS. 6A and 6B and the glass capillary 20 shown in FIGS. 7A and 7B, the glass is preferably silicate glass having a total iron content ($Fe_2O_3$+FeO) of no more than 1000 ppm. As a result, absorption loss of the laser beam can be reduced.

Figure 8:
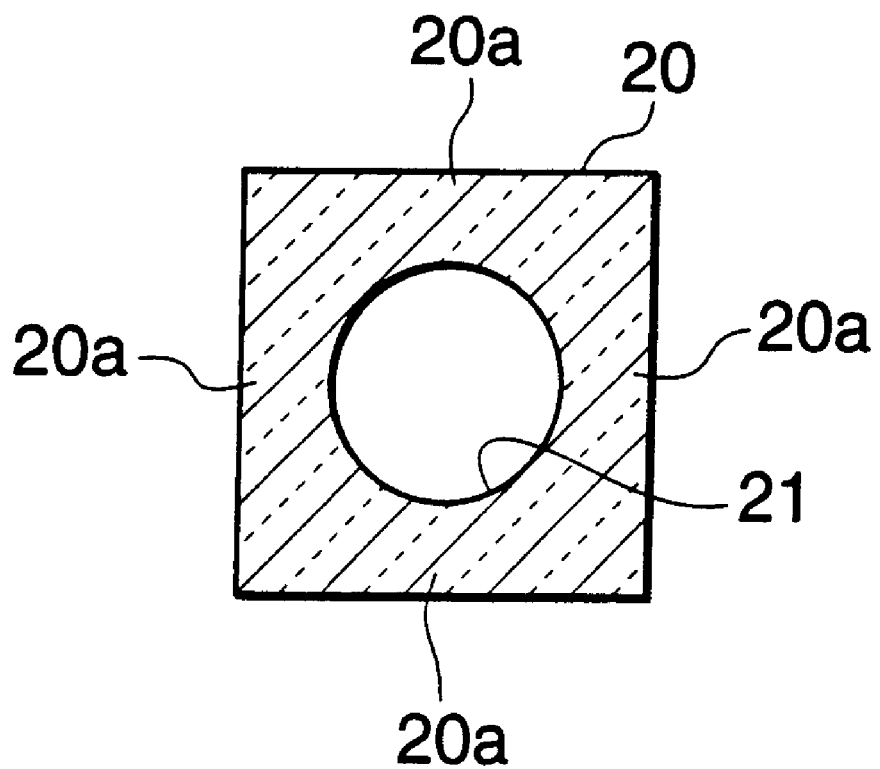
FIG. 8 is a cross-sectional view useful in explaining the cross-sectional shapes of a glass capillary 20 and an internal hole 21 formed therein.

It should also be noted that the present invention can be applied not only to glass capillaries 20 such as those of FIGS. 6A and 6B and FIGS. 7A and 7B, but also, for example, to a glass capillary 20 having a rectangular cross section and having formed therein an internal hole 21 having a circular cross section, as shown in FIG. 8.

Glass capillaries 20 as described above are arranged in a DNA analyzer with the thin-walled portions 20a of the glass capillaries 20 positioned in the path of the laser beam.

When glass capillaries 20 as described above are used in an electrophoretic DNA analyzer, each glass capillary 20 is placed such that the surfaces of the thin-walled portions 20a thereof are perpendicular to the laser beam, and hence scattering of the laser beam at the surfaces of the glass capillaries 20 can be prevented and the detection efficiency of the electrophoretic DNA analyzer can be increased; furthermore, the analyzer can be given a simple structure.

What is claimed is:

1. A glass capillary array for fluorescence analysis, comprising:
    a plurality of glass capillaries each having a rectangular cross section and having an internal hole formed therein, said plurality of glass capillaries being arranged in a row along a direction of irradiation of a laser beam for fluorescence analysis;
    wherein the glass capillary array has a fluorescence analysis section comprising a portion of each of said glass capillaries positioned in a region including an optical axis of the laser beam and a vicinity thereof,
    and said glass capillaries are joined together substantially into a single body using a transparent material in at least the fluorescence analysis section.

2. A glass capillary array for fluorescence analysis as claimed in claim 1, wherein the difference between a refractive index of the transparent material and a refractive index of a mother glass of said glass capillaries is not more than 0.3.

3. A glass capillary array for fluorescence analysis as claimed in claim 2, wherein the difference between the refractive index of the transparent material and the refractive index of the mother glass of said glass capillaries is not more than 0.3, and the number of said glass capillaries joined together is in a range of 10 to 30.

4. A glass capillary array for fluorescence analysis as claimed in claim 2, wherein the difference between the refractive index of the transparent material and the refractive index of the mother glass of said glass capillaries is not more than 0.2, and the number of said glass capillaries joined together is in a range of 10 to 100.

5. A glass capillary array for fluorescence analysis as claimed in claim 1, wherein said glass capillaries are joined together using a resin adhesive.

6. A glass capillary array for fluorescence analysis as claimed in claim 1, wherein said glass capillaries are joined together using glass frit.

7. A glass capillary array for fluorescence analysis as claimed in claim 1, wherein said glass capillaries are joined together by welding using a laser beam.

8. A method of manufacturing a glass capillary array for fluorescence analysis, comprising the steps of:
    arranging a plurality of glass capillaries, each having a rectangular cross section and having an internal hole formed therein, in a row along a direction of irradiation of a laser beam for fluorescence analysis, to form a glass capillary array having a fluorescence analysis section comprising a portion of each of said glass capillaries positioned in a region including an optical axis of the laser beam and a vicinity thereof; and
    joining the glass capillaries together substantially into a single body using a transparent material in at least the fluorescence analysis section.

9. A method as claimed in claim 8, wherein the glass capillaries are joined together using a resin adhesive.

10. A method as claimed in claim 8, wherein the glass capillaries are joined together using glass frit.

11. A method as claimed in claim 8, wherein the glass capillaries are joined together by welding using a laser beam.

* * * * *